(12) United States Patent
Shingte et al.

(10) Patent No.: US 11,919,834 B2
(45) Date of Patent: Mar. 5, 2024

(54) METHOD OF MAKING PERFLUOROCYCLOBUTANE-CONTAINING MONOMER

(71) Applicant: SOLVAY SPECIALTY POLYMERS ITALY S.P.A., Bollate (IT)

(72) Inventors: Rahul Shingte, Gujarat (IN); Debaki Ghosh, Gujarat (IN); Letanzio Bragante, Due Carrare (IT); Manuel Gregori, Rovellasca (IT); Stefano Millefanti, Tradate (IT); Emanuela Antenucci, Saronno (IT); Joel Pollino, Johns Creek, GA (US)

(73) Assignee: SOLVAY SPECIALTY POLYMERS ITALY S.P.A., Bollate (IT)

(*) Notice: Subject to any disclaimer, the term of this patent is extended or adjusted under 35 U.S.C. 154(b) by 0 days.

(21) Appl. No.: 17/604,522

(22) PCT Filed: May 5, 2020

(86) PCT No.: PCT/EP2020/062443
§ 371 (c)(1),
(2) Date: Oct. 18, 2021

(87) PCT Pub. No.: WO2020/229227
PCT Pub. Date: Nov. 19, 2020

(65) Prior Publication Data
US 2022/0194885 A1 Jun. 23, 2022

(30) Foreign Application Priority Data
May 10, 2019 (IN) .............................. 201921018845

(51) Int. Cl.
| | |
|---|---|
| C07C 43/275 | (2006.01) |
| C07C 41/06 | (2006.01) |
| C07C 41/30 | (2006.01) |
| C07C 51/08 | (2006.01) |
| C07C 201/08 | (2006.01) |
| C07C 213/02 | (2006.01) |
| C07C 253/14 | (2006.01) |
| C07C 317/22 | (2006.01) |
| C07D 263/57 | (2006.01) |
| C08G 73/10 | (2006.01) |

(52) U.S. Cl.
CPC ............ *C07C 213/02* (2013.01); *C07C 41/06* (2013.01); *C07C 41/30* (2013.01); *C07C 51/08* (2013.01); *C07C 201/08* (2013.01); *C07C 253/14* (2013.01); *C07C 317/22* (2013.01); *C07D 263/57* (2013.01); *C08G 73/1007* (2013.01); *C07C 2601/04* (2017.05)

(58) Field of Classification Search
None
See application file for complete search history.

(56) References Cited

U.S. PATENT DOCUMENTS

| | | | | |
|---|---|---|---|---|
| 4,734,460 A | | 3/1988 | Yamada | |
| 5,021,602 A | * | 6/1991 | Clement | ................. C07C 69/92 564/453 |
| 5,198,513 A | * | 3/1993 | Clement | ................. C07C 49/84 526/248 |
| 5,210,265 A | * | 5/1993 | Clement | ................. C07C 45/70 568/839 |
| 5,442,030 A | * | 8/1995 | Yang | ................. C08G 73/1078 528/229 |

FOREIGN PATENT DOCUMENTS

| | | | |
|---|---|---|---|
| CN | 107580613 A | 1/2018 | |
| CN | 108290985 A | 7/2018 | |
| JP | 2000264966 A | 9/2000 | |
| WO | 9015042 A2 | 12/1990 | |
| WO | WO-2013031603 A1 * | 3/2013 | ............ C09K 19/20 |
| WO | 2016180660 A1 | 11/2016 | |
| WO | 2017046379 A1 | 3/2017 | |

OTHER PUBLICATIONS

Y. Zhou et al., 129 Journal of Fluorine Chemistry, 498-502 (2008) (Year: 2008).*
W. Yao et al., 5 Polymer Chemistry, 6334-6343 (2014) (Year: 2014).*
Iacono S. T. et al., "Science and Technology of Perfluorocyclobutyl Aryl Ether Polymers", J. Polym. Sci. Part A: Polym. Chem., 2007, vol. 45, p. 5705-5721—Wiley Periodicals Inc.
Zhou Y. et al., "Novel fluorinated poly(aryl ether)s derived from 1,2-bis(4-(4-fluorobenzoyl)phenoxy)-hexafluorocyclobutane", Journal of Fluorine Chemistry, 2008, vol. 129, p. 498-502—Elsevier B.V.
Li Y. et al., "Perfluorocyclobutyl-based methacrylate monomers: Synthesis and radical polymerization", 2009, vol. 130, p. 354-360—Elsevier B.V.

* cited by examiner

*Primary Examiner* — Alexander R Pagano
(74) *Attorney, Agent, or Firm* — Osha Bergman Watanabe & Burton LLP

(57) ABSTRACT

The invention pertains to a multi-step process for making polyfunctional aromatic compounds comprising two phenyl rings bearing reactive groups susceptible of polycondensation reaction to provide polycondensed polymers, said method using economic raw materials, and possessing high selectivity and overall yield.

13 Claims, No Drawings

METHOD OF MAKING PERFLUOROCYCLOBUTANE-CONTAINING MONOMER

CROSS-REFERENCE TO RELATED APPLICATION

This application is a U.S. national stage entry under 35 U.S.C. § 371 of International Application No. PCT/EP2020/062443 filed May 5, 2020, which claims priority to Indian Provisional Application No. 201921018845, filed on May 10, 2019. The entire contents of these applications are explicitly incorporated herein by this reference.

TECHNICAL FIELD

The invention pertains to a method of making perfluorocyclobutane-containing monomer, to certain perfluorocyclobutane-containing monomers therefrom, and to method of using the same for making polymers.

BACKGROUND ART

Perfluorocyclobutyl (PFCB) aryl ether polymers have been extensively investigated in the past, as resulting either from the thermal [2π+2π]cyclodimerization of aryl trifluorovinylether monomers or from condensation polymerization of perfluorocyclobutyl aryl ether dimer difunctional intermediates, as explained notably in IACONO, Scott T., et al. Science and Technology of Perfluorocyclobutyl Aryl Ether Polymers. *J. Polym. Sci. Part A: Polym. Chem.* 2007, vol. 45, no., p. 5705-5721.

In this domain, one of the critical aspects for the success of approaches based on PFCB aryl ether polymers is the provision of monomers and intermediates possessing suitable purity for being used in polycondensation reactions through an economically viable methodology, using possibly easily available and inexpensive chemicals as raw materials, and applying high yield/high selectivity chemical reactions.

For instance, U.S. Pat. No. 5,021,602 (THE DOW CHEMICAL COMPANY) Apr. 6, 1991 describes a method for preparing a compound of formula:

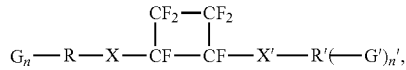

with R and R' being groups linked through molecular structures X and X' to the perfluorocyclobutane ring, in particular R and R' being phenylene groups and X and X' being ethereal —O— moieties; G and G' being any reactive group, with n and n' being integers, said compounds being prepared by dimerization of functional perfluorovinyl compounds of formula $G_n$-R—X—CF=$CF_2$, whereas these latter compounds are formed preferably by a method comprising the steps of:
(a) forming a salt having an anion of formula: $(G'')_n$-R—X—, with G" being a functional group G or a group susceptible of being modified to yield group G;
(b) reacting said salt with a 1,2-dihalo-1,1,2,2-tetrafluoroethane of formula Q-$CF_2$—$CF_2$-Q, with at least one Q being iodine or bromine, and the remainder being chlorine, iodine or bromine, so as to obtain a compound of formula $(G'')_n$-R—X—$CF_2$—$CF_2$-Q; and
(c) dehalogenating this latter compound in the presence of a metallic reagent, such as Zn or Mg.

The method for introducing the trifluorovinyl group in the precursor to the perfluorocyclobutyl derivative involves the use of expensive halo/fluoroderivatives in a sequence of nucleophilic substitution and subsequent dehalogenation, which may affect overall yield of the method, and which may lead to the presence of bromine/iodine containing side products in the final perfluorocyclobutyl derivative which may negatively impact reactivity of the same as a monomer, and/or the properties/thermal stability of polymers obtained therefrom.

An alternative approach leading to perfluorocyclobutane-containing compounds, where the said PFCB ring is bound through a C—C bond directly to the aromatic carbons of an adjacent phenyl ring is provided in U.S. Pat. No. 5,442,030 (E.I. DUPONT DE NEMOURS AND COMPANY) 15 Aug. 1995. In this document, by reacting para- or meta-nitroiodobenzene with the resulting product of addition of Zn to iodotrifluoroethylene under Pd(PΦ$_3$)$_4$ catalysis, corresponding trifluorovinyl compounds of formula $CF_2$=CF-Φ-$NO_2$ are obtained, with Φ being phenyl group, which are dimerized to $O_2$N-Φ-PFCB-Φ-$NO_2$ (whereas PFCB is perfluorocyclobutane), and then transformed into amino compounds by reduction with $SnCl_2$/$NaBH_4$. Nevertheless, the electro-withdrawing effect exercised by the nitro group on the PFCB moiety directly bound to the aromatic carbons lead to at least partial defluorination of the PFCB group, so leading to a perfluorocyclobutene moiety.

There still remains a need in the art for efficient methods of making perfluorocyclobutyl-diarylether monomers, starting from easily and economically accessible precursors and leading to compounds endowed with high purity with high yields.

SUMMARY OF INVENTION

The invention hence pertains to a method for manufacturing a compound of general formula [formula (I)]:

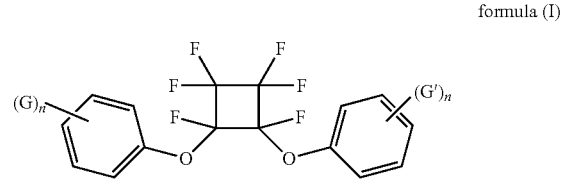

formula (I)

wherein each of G and G', equal to or different from each other, is independently selected from the group consisting of
halogens selected from F, Cl, Br, I, in particular from —F, —Cl;
—$NR_H^1R_H^2$, with $R_H^1$ and $R_H^2$ being independently H or a $C_1$-$C_6$ hydrocarbon group, preferably being H;
—OH;
nitrile group of formula —CN and nitro group of formula —$NO_2$;
—COY, with Y being —X, with X being a halogen selected from F, Cl, Br, I, in particular —F, —Cl; —OH; —$OR_H^3$, —$NR_H^1R_H^2$, with $R_H^3$ being a $C_1$-$C_{12}$ hydrocarbon group, in particular a $C_1$-$C_6$ alkyl or a $C_6$-$C_{12}$ aryl group; and $R_H^1$ and $R_H^2$ having the meaning detailed above; preferably Y being OH;

—SO$_2$Y', with Y' being —OH, or being —X', with X' being a halogen selected from F, Cl, Br, I, in particular —F, —Cl;

E-Ar—X", with X" being hydrogen, —OH, —X$^{oo}$, —C(O)X$^{\#}$ with X$^{\#}$ being —OH, or being —X$^{oo}$; with X$^{oo}$ being a halogen selected from F, Cl, Br, I, in particular —F, —Cl; -E- being a divalent bridging group selected from the group consisting of a bond, a C$_1$-C$_6$ carbon-containing bridging group; a sulphur-containing bridging group; exemplary embodiments of -E- are notably: —(CH$_2$)$_m$—, with m being an integer of 1 to 3; —C(O)—, —C(CH$_3$)$_2$—, and —SO$_2$—; —Ar— being a divalent aromatic group, in particular a (optionally substituted) phenyl group (-Ph-), e.g. whereas the linking bonds in -Ph- may be in ortho, meta or para position with respect to each other, preferably in para position, a group of formula

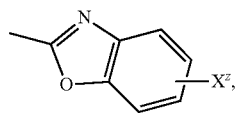

with X$^z$ being —NH$_2$; —NO$_2$; —OH, —X$^{oo}$, —C(O)X$^{\#}$ with X$^{\#}$ being —OH, or being —X$^{oo}$; with X$^{oo}$ being a halogen selected from F, Cl, Br, I, in particular —F, —Cl;

each of n, equal to or different from each other, is an integer of 1 to 3, preferably 1 to 2, more preferably n=1, sand method comprising:

Step (a): a step of reacting an anion of formula [formula (II)]:

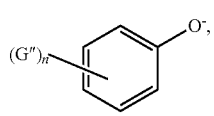

wherein G" is a group G or G', as described above, or is a precursor thereof, with tetrafluoroethylene at a temperature of at most 115° C. and at a pressure of at least 4 bar, so as to obtain a compound of formula [formula (III)]:

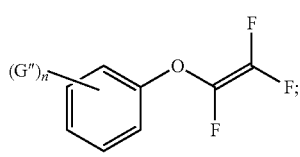

Step (b): a step of dimerizing at least one compound of formula (III) obtained from step (a) by thermal treatment at a temperature exceeding 150° C., so as to obtain a compound of formula [formula (IV)]:

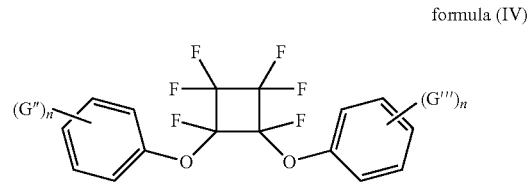

wherein each of G" and G'" is a group G or G', as described above, or is a precursor thereof, being understood that when G" and G'" are a group G or G' as detailed above, compound of formula (IV) qualifies as a compound of formula (I); and Step (c): optionally, a step of reacting compound of formula (IV) in appropriate conditions to transform precursor groups G" and G'" of formula (IV) into groups G and G' so as to obtain compound of formula (I) above.

The Applicant has surprisingly found that the method described above is effective in providing in high yields compounds (I), as above detailed, which are notably useful as monomers for polycondensation reactions, using, as synthon for the perfluorocyclobutane group, inexpensive and readily available tetrafluoroethylene, said method providing the target compounds in high yields and exempt from brominated and iodinated impurities having the said halogens in the perfluorocyclobutane ring.

DESCRIPTION OF EMBODIMENTS

As said, the method of the present invention serves to produce compounds of formula (I), as above detailed, which, as detailed above, comprises on each phenyl ring of the said formula (I) at least one functional group G or G'. While more than one functional group may be present, it is generally acknowledged that best performances are obtained when each of n is 1, that is to say that formula (I) possesses only one functional group on each phenyl ring.

As said, G and G' are independently selected from the functional moieties listed above, which advantageously can be leveraged for polymerizing compound (I) in polycondensation or other types of reaction, or further modifying the same, in view of the possible incorporation into a polymer chain.

The choice of the nature of the group G or G' will depend upon the use of the molecule (1): in particular, as compounds of formula (I) have been shown to possess utility as monomers for incorporation in polycondensation polymers, the nature of the said groups will depend upon the targeted nature of the said polycondensation polymer.

For instance, when monomers suitable for incorporation into polyimide, polyamide, polyamideimide structures are sought, in compound of formula (I), G and G' may advantageously be —NR$_H^1$R$_H^2$, with R$_H^1$ and R$_H^2$ being independently H or a C$_1$-C$_6$ hydrocarbon group, preferably being H;

—a group of formula

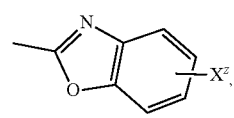

with X$^z$ being —NH$_2$.

When monomers suitable for incorporation into polyamide, polybenzoxazole, polyester structures are sought, G and G' may advantageously be:
- a —COY group, with Y being —X, with X being a halogen selected from F, Cl, Br, I, in particular —F, —Cl; —OH; —OR$_H^3$, —NR$_H^1$R$_H^2$, with R$_H^3$ being a C$_1$-C$_{12}$ hydrocarbon group, in particular a C$_1$-C$_6$ alkyl or a C$_1$-C$_{12}$ aryl group; and R$_H^1$ and R$_H^2$ having the meaning detailed above; preferably Y being OH;
- a nitrile group of formula —CN; or
- —OH.

When monomers suitable for incorporation into polyarylether structures are sought, G and G' may advantageously be —OH; a group of formula —SO$_2$Y', with Y' being —OH, or being —X', with X' being a halogen selected from F, Cl, Br, I, in particular —F, —Cl or a halogen selected from F, Cl, Br, I, in particular from —F, —Cl; or a group -E-Ar—X", as detailed above.

In particular, when monomers specifically suitable for incorporation into polyarylether sulfone structures are sought, G and G' may be selected from groups of formula —SO$_2$Y', with Y' being —OH, or being —X', with X' being a halogen selected from F, Cl, Br, I, in particular —F, —Cl; and from groups -E-Ar—X", as detailed above, with E being —SO$_2$—, and X" being —OH or a halogen selected from F, and Cl.

Generally, hence the method of the invention will be used for manufacturing compounds of formula (Ia):

formula (Ia)

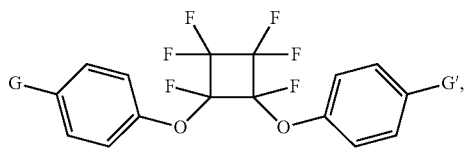

with G and G' in para positions on the aromatic rings. It is also further preferred for compounds of formula (Ia) that G and G' are identical.

Certain compounds of formula (I) as above detailed are novel, and are further objects of the present invention. In particular, compounds of formula (I) (and preferably of formula (Ia)) with G and G' being:
(A) —a group of formula -E-Ar—X", with X" being hydrogen, —OH, —X$^{oo}$, —C(O)X$^\#$ with X$^\#$ being —OH, or being —X$^{oo}$; with X$^{oo}$ being a halogen selected from Cl, Br, I, in particular —Cl; -E- being a divalent bridging group selected from the group consisting of a bond, a C$_1$-C$_6$ carbon-containing bridging group or a sulphur-containing bridging group (exemplary embodiments of -E- being notably: —(CH$_2$)$_m$—, with m being an integer of 1 to 3; —C(O)—, —C(CH$_3$)$_2$—, and —SO$_2$—); or
(B) —a group of formula

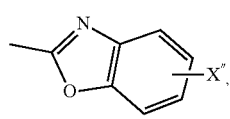

with X" being hydrogen, —OH, —X$^{oo}$, —C(O)X$^\#$ with X$^\#$ being —OH, or being —X$^{oo}$; with X$^{oo}$ being a halogen selected from F, Cl, Br, I, in particular —F, —Cl;
are an additional object of the present invention.

Exemplary embodiments of the compounds of the present invention are notably:

Compound (I-i) of formula:

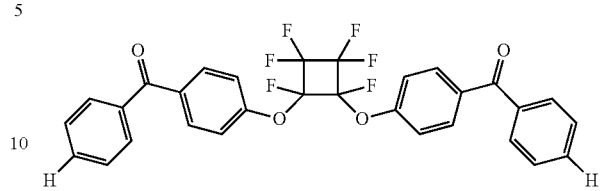

Compound (I-ii) of formula:

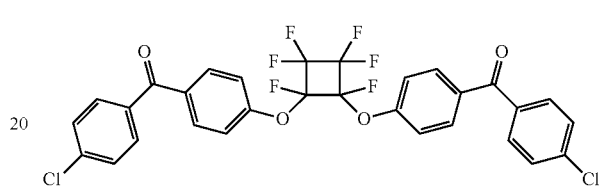

Compound (I-ii) of formula:

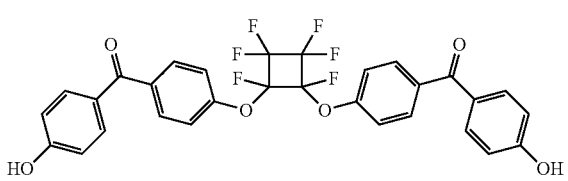 [SMILES: O=C(c1ccc(O)cc1)c1ccc(OC2(F)C(F)(F)C(F)(F)C2(F)Oc2ccc(C(=O)c3ccc(O)cc3)cc2)cc1]

Compound (I-iv) of formula:

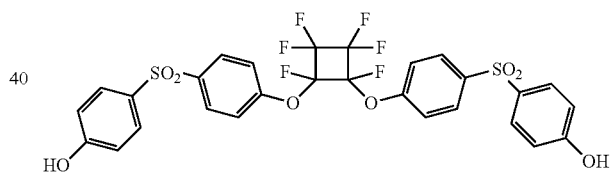

Compound (I-v) of formula:

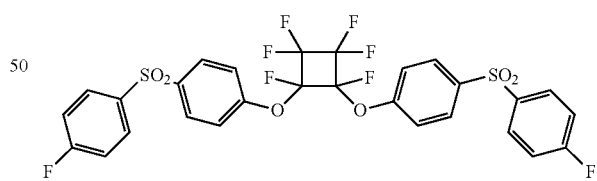

Compound (I-vi) of formula:

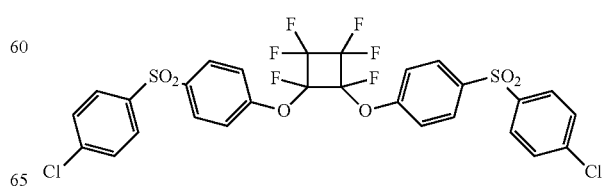

Compound (I-vii) of formula:

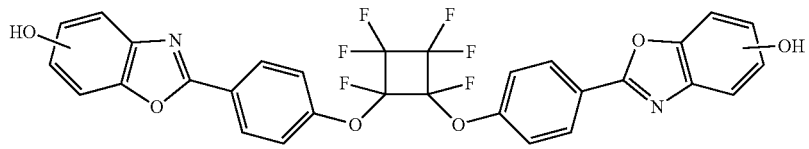

Compound (I-viii) of formula:

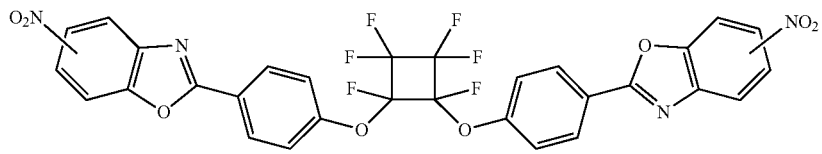

Compound (I-ix) of formula:

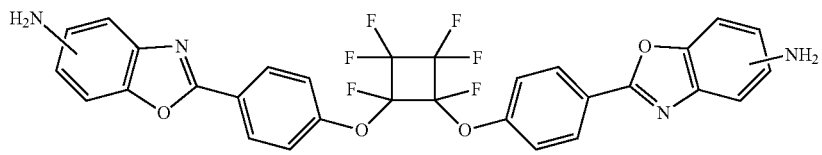

Compound (I-x) of formula:

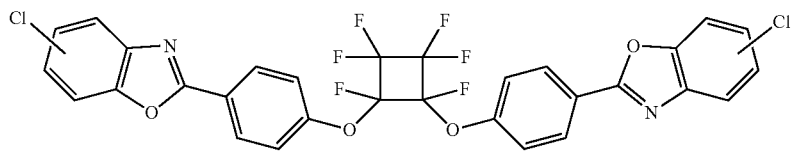

Compound (I-xi) of formula:

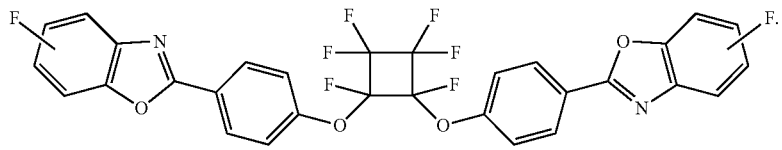

All these compounds may be used as monomers/precursors for the manufacture of polyaryletherketones, polyarylether sulphones, benzooxazole, polyimide and the like.

As said, in first step of the present invention, an anion of formula (II) is reacted with tetrafluoroethylene.

As said, in compound of formula (II), G" is a group of formula G or G', as described above, or is a precursor thereof. This latter expression is to be construed to mean that, when group G" is different from the group G and G' targeted in the method of the invention, a precursor group is meant to represent a group which, through appropriate chemistry, can be transformed into the target group G or G' of formula (I).

When G" is a group G or G', the method of the invention leads through the sequence of Step (a) and Step (b) to the target product of formula (I), as above detailed.

Exemplary embodiment's of G" groups according to this variant are notably halogens selected from F, Cl, Br, I, in particular from —F, —Cl.

When G" is different from group G and G', the choice of group G" will hence depend upon the target group G/G' intended to be comprised in the compound (I) to be prepared, and the functionalization chemistry underlying Step (c), which hence becomes a mandatory additional step of the method of the present invention.

Exemplary embodiment's of G" groups according to this variant are notably:

hydrogen;
halogens selected from F, Cl, Br, I, in particular from —F, —Cl;
$C_1$-$C_3$ alkyl group, in particular methyl group (—$CH_3$);
$C_1$-$C_3$ alkoxy groups, in particular groups of formula —$OR_{alk}$, with $R_{alk}$ being a $C_1$-$C_3$ alkyl group, in particular a group of formula —$OCH_3$.

When G" is a hydrogen, Step (c) advantageously comprises at least one step selected from the group consisting of:
a step (C-1) of electrophilic aromatic substitution, whereas said hydrogen G" atom is reacted preferably in the presence of a Lewis acid, with an electrophile selected from the group consisting of:
(i) a X—$R'_{hyc}$ reactant, with X=Cl, Br, bound to a $sp^3$-hybridized carbon of $R'_{hyc}$ group, and $R'_{hyc}$ being a $C_1$-$C_{18}$ possibly substituted hydrocarbon group including said $sp^3$-hybridized carbon, which may comprise one or more of groups of formula: —$(CH_2)_m$—, with m being an integer of 1 to 3; —C(O)—, —$C(CH_3)_2$—, and —$SO_2$—, and which may comprise one or more aromatic groups; this reaction may lead to compounds of formula (I) having groups G/G' of formula —$R_{hyc}$, as detailed above; oxidation of the pendant $R'_{hyc}$ group may lead to compounds of formula (I) having groups G/G' of formula —COY as detailed above; appropriate choice of $R'_{hyc}$ group may lead to compounds of formula (I) having groups G/G' of formula -E-Ar—X" as detailed above, with -E- comprising a $sp^3$-hybridized carbon;
(ii) a X—C(O)—$R''_{hyc}$ reactant, with X=Cl, Br, and $R''_{hyc}$ being a $C_1$-$C_{18}$ possibly substituted hydrocarbon group, which may comprise one or more of groups of formula: —$(CH_2)_m$—, with m being an integer of 1 to 3; —C(O)—, —$C(CH_3)_2$—, and —$SO_2$—, and which may comprise one or more aromatic groups; this reaction may lead to compounds of formula (I) having groups G/G' of formula —C(O)—$R''_{hyc}$, as detailed above; appropriate choice of $R''_{hyc}$ group may lead to compounds of formula (I) having groups G/G' of formula -E-Ar—X" as detailed above, with -E- being a —C(O)— group;
(iii) a X—$SO_2$—$R*_{hyc}$ reactant, with X=Cl, Br, and $R*_{hyc}$ being a $C_1$-$C_{18}$ possibly substituted hydrocarbon group, which may comprise one or more of groups of formula: —$(CH_2)_m$—, with m being an integer of 1 to 3; —C(O)—, —$C(CH_3)_2$—, and —$SO_2$—, and which may comprise one or more aromatic groups; preferably a X—$SO_2$—$R*_{Ar}$, whereas $R*_{Ar}$ is a $C_6$-$C_{18}$ possibly substituted aromatic group; this reaction may lead to compounds of formula (I) having groups G/G' of formula -E-Ar—X" as detailed above, with -E- being a —$SO_2$— group;
a step (C-2) of sulfonation, in particular with concentrated sulfuric acid or chlorosulphonic acid, which would lead to compounds of formula (I) having groups G/G' of formula —$SO_2Y'$, as detailed above; sulfonation reaction, preferably with oleum, concentrated sulphuric acid or Cl—$SO_2$—OH may lead to compounds of formula (I) having groups G/G' of formula —$SO_3H$ or —$SO_2Cl$, which may be further functionalized to provide for compounds of formula (I) having groups G/G' of formula -E-Ar—X", with E=—$SO_2$—, as detailed above;
a step (C-3) of nitration, in particular with nitronium ion, e.g. generated in situ by reaction of concentrated sulfuric and nitric acid, which would lead to compounds of formula (I) having groups G/G' of formula —$NO_2$,
as detailed above; this step may be possibly followed by a step of reduction of so-generated —$NO_2$ groups, may lead to compounds of formula (I) having groups G/G' of formula —$NR_H^1R_H^2$, as detailed above.

When G" is a halogen selected from F, Cl, Br, I, in particular from —F, —Cl, Step (c) comprises advantageously at least one step selected from the group consisting of:
a step (C-4) of nucleophilic substitution, by reaction with:
(j) an alkali hydroxide (NaOH, KOH . . . ), so as to obtain a compound of formula (I) with G/G' being —OH;
(jj) a CN-containing compound (NaCN, KCN, $K_4[Fe(CN)_6]$ . . . ), leading to the corresponding CN-substituted compound, which (jj-1) can be hydrolysed to provide for compounds of formula (I) whereas G/G' are groups of formula —COY, as detailed above, or (jj-2) maybe reacted with an ortho-amino-phenol derivative of formula

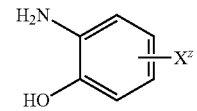

so as to provide for compounds of formula (I) whereas G/G' are groups of formula

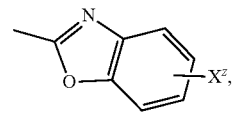

with $X^z$ being —$NH_2$; —$NO_2$; —OH, —$X^{oo}$, —C(O)$X^\#$ with $X^\#$ being —OH, or being —$X^{oo}$; with $X^{oo}$ being a halogen selected from F, Cl, Br, I, in particular —F, —Cl;
(jjj) an alkali (alkyl)amide ($KNH_2$, $NaNH_2$ . . . ), leading to compounds of formula (I) whereas G/G' are groups of formula —$NR_H^1R_H^2$, as detailed above;
a step (C-5) of reaction with Mg or Li, to form corresponding organo-magnesium or organo-lithium compounds of formula (I) whereas G/G' are groups of formula —$MgX^{Mg}$ or —Li, with $X^{Mg}$ being a halogen, preferably Cl or Br, which can be further reacted for generating derivatives of formula (I) whereas G/G' are groups of formula -E-Ar—X", as above detailed, with X" being hydrogen or halogen, as above detailed, Preferably hydrogen.

When G" is a $C_1$-$C_3$ alkyl group, Step (c) advantageously comprises at least one step selected from the group consisting of:
a Step (C-6) of oxidation, e.g. in the presence of $KMnO_4$, to provide for compounds of formula (I) whereas G/G' are groups of formula —COY, as detailed above; said groups of formula —COY, as detailed above maybe reacted with an ortho-amino-phenol derivative of formula

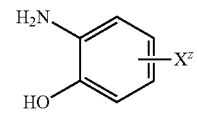

so as to provide for compounds of formula (I) whereas G/G' are groups of formula

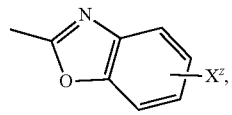

with $X^z$ being —$NH_2$; —$NO_2$; —OH, —$X^{oo}$, —C(O) $X^\#$ with $X^\#$ being —OH, or being —$X^{oo}$; with $X^{oo}$ being a halogen selected from F, Cl, Br, I, in particular —F, —Cl.

When G" is a $C_1$-$C_3$ alkoxy group, Step (c) advantageously comprises at least one step selected from the group consisting of:
 a Step (C-7) of hydrolysis, e.g. in the presence of acetic acid/hydrobromic acid, so as to provide for compounds of formula (I) whereas G/G' are groups of formula —OH.

Providing an anion of formula (II) can be effected by reacting corresponding phenol derivative of formula (Iip) with a base:

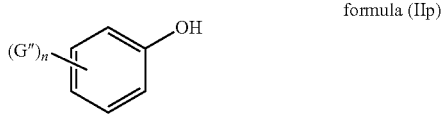

formula (Iip)

wherein n and G" have the same meaning as indicated above.

Generally, mono-substituted phenol bearing a group G" in para position would be preferred.

Whichever base can be used for extracting the acidic proton from compound of formula (Iip); in particular hydroxides of alkali metal or alkali metal earth could be used. While the reaction between compound of formula (Iip) and the base may be carried out in an aqueous medium, compound (II) is generally provided in Step (a) of the method of the present invention in substantially anhydrous form, i.e. in a form comprising an amount of residual water of less than 500 ppm, preferably less than 200 ppm, even more preferably less than 50 ppm.

Step (a) is generally carried out in the presence of a polar organic solvent; in particular ethereal solvents have been found particularly effective, enabling suitable solubilisation of compound of formula (II), while possessing adequate solvation and $pK_a$ properties for favouring the substitution reaction leading to the corresponding trifluorovinyl ether derivative, over notably the addition reaction leading to a —O—$CF_2$—$CF_2$—H substitution or even the formation of other higher molecular weight derivatives. Among aliphatic ethers, polar organic solvents which have been found particularly effective in Step (a) are notably diethyl ether, dipropyl ether, diisopropyl ether, dibutyl ether, methyltertiobutylether, dipentyl ether, diisopentyl ether, ethylene glycol dimethyl ether, ethylene glycol diethyl ether, ethylene glycol dibutyl ether, di-ethylene glycole di methyl ether; dioxane, tetrahydrofuran (THF), with THE being particularly preferred. Mixture of one or more of the above solvents may be used.

In Step (a), reaction temperature is kept at a temperature of at most 115° C., preferably of at most 110° C., even more preferably of at most 100° C. Lower boundary for reaction temperature in Step (a) is generally adjusted so as to achieve reasonable reaction kinetics; a temperature of at least 45° C., preferably of at least 55° C. will be hence generally preferred.

In Step (a), reaction pressure is of at least 4 bar, preferably at least 4.5 bar, even more preferably at least 5 bar. Upper boundary for reaction pressure in Step (a) is generally adjusted for practical reason to below 30 bar, typically below 27 bar, even more preferably 25 bar. Generally, in Step (a) an excess of gaseous tetrafluoroethylene (TFE) may be fed so as to generate an initial reaction pressure, and then having said pressure gradually decrease as the TFE is reacting; or, subsequent additions of TFE, either continuously or stepwise, may be effected for counterbalancing the pressure drop because of the progresses of the TFE conversion. Maintaining a pressure of above 4 bar at a substantially constant set-point pressure value by addition, preferably continuous addition, of TFE has been found as a preferred embodiment for controlling selectivity of the reaction, and maintaining substantially constant reaction conditions throughout Step (a).

The method of the present invention includes a Step (b) of dimerizing at least one compound of formula (III) obtained from Step (a) by thermal treatment at a temperature exceeding 150° C. Generally, in target compound (I), groups G and G' are identical, so that it is preferably for Step (b) to be carried out using only one compound of formula (III), as detailed above. This being said, alternatives whereas a mixture of two different compounds of formula (III) are used are also encompassed; resulting dimerization product being hence a mixture of compounds leading variable groups G" and G'''.

Reaction in Step (b) is generally carried out under inter atmosphere, generally under nitrogen atmosphere. A pressure of exceeding atmospheric pressure, e.g. a pressure of 1.5, preferably 2.0, even more preferably 2.5 bar may be preferred. Reaction temperature is generally of at least 155° C., preferably of at least 160° C. While higher temperatures may favour kinetics of dimerization, temperatures of less than 210° C., preferably less than 205° C., even more preferably less than 200° C. are preferred for minimizing side-reactions, e.g. leading to decomposition compounds.

As explained above, the method of the invention may or may not comprise a further step (C).

According to a first embodiment of the invention, compound of formula (II) is a phenol salt (that is to say G'''=H), and the method of the invention comprises a further Step (1-C) of reacting G'''=H to provide for compound (I), with groups G/G' selected among the groups listed above.

According to a first variant, the method of the invention comprises reacting in Step (a) a compound of formula (II) with G" being a precursor of G/G' and G'''=H, and said method comprises a Step (1V-C) comprising:
 a Step (1V-C-1) of reacting compound of formula (IV) with G'''=H under electrophilic nitration conditions, generally in the presence of $HNO_3$/$H_2SO_4$, so as to obtain a compound of formula (I) with G and G'=—$NO_2$;
 a Step (1V-C-2) of reacting said compound under reductive conditions, e.g. un the presence of hydrazine and Pd/C catalyst, so as to obtain a compound of formula (I) with G and G' being —$NH_2$.

According to a second variant, the method of the invention comprises reacting in Step (a) a compound of formula (II) with G" being a precursor of G/G' and G" being selected from the group consisting of halogens selected from F, Cl, Br, I, in particular from —F, —Br, —Cl, and said method comprises a Step (2V-C) comprising:
- a Step (2V-C-1) of reacting compound of formula (IV) with G" being selected from the group consisting of halogens selected from F, Cl, Br, I, in particular from —F, —Br, —Cl with a compound of formula MeNH$_2$, with Me being a mono-valent metal cation in the presence of ammonia, so as to obtain a compound of formula (I) with G and G' being —NH$_2$.

Depending upon starting material of formula (II), compound of formula (I) may be a mixture of positional isomers, with G and G'-NH$_2$ groups being independently in ortho, meta or para position on each of the phenyl rings of compound (I).

According to a third variant, the method of the invention comprises reacting in Step (a) a compound of formula (II) with G" being equal to G/G' and G" being selected from the group consisting of halogens selected from F, Cl, Br, I, in particular from —F, —Br, —Cl, so as to obtain a compound of formula (I) with G and G' being a halogen selected from F, Cl, Br, I; which method notably:
- does not advantageously include any Step (C), as target compound (I) is a compound whereas G and G' are halogens; and
- is preferably a method whereas n=1, and G/G'/G" are in para position with respect to the oxygen atom in compounds (I) and (II).

According to a fourth variant, the method of the invention comprises reacting in Step (a) a compound of formula (II) with G" being a precursor of G/G' and G"=H, and said method comprises a Step (4V-C) comprising:
- a Step (4V-C-1) of reacting compound of formula (IV) with G"=H under electrophilic sulfonation reaction, notably with concentrated H$_2$SO$_4$ or with a halosulphonic acid so as to obtain a compound of formula (I) with G/G' being a group —SO$_2$Y', with Y' being —OH, or being —X', with X' being a halogen selected from F, Cl, Br, I, in particular —F, —Cl;
- optionally, a Step (4V-C-2) of halogenating said compound of formula (IV) so as to obtain corresponding compound whereas Y' in groups —SO$_2$Y' is —Br, —Cl, or —F;
- a Step (4V-C-3) of reacting the so obtained compound of formula (I) with G/G' being a group —SO$_2$Y' with an aromatic compound of formula Ar—X$^o$ under electrophilic substitution conditions, with X$^o$ being hydrogen, or a halogen selected from F, Cl, Br, I, in particular —F, —Cl, so as to obtain a compound of formula (I), with G/G' being a group of formula -E-Ar—X", as detailed above.

According to a fifth variant, the method of the invention comprises reacting in Step (a) a compound of formula (II) with G" being a precursor of G/G' and G" being a hydrogen atom (G"=H), and said method comprises a Step (5V-C) comprising:
- a Step (5V-C-1) of reacting compound of formula (IV) with G"=H with a X—R'$_{hyc}$ reactant, with X=Cl, Br bound to a sp$^3$-hybridized carbon of R'$_{hyc}$ group, and R'$_{hyc}$ being a C$_1$-C$_{18}$ possibly substituted hydrocarbon group including said sp$^3$-hybridized carbon, which comprises one or more of groups of formula: —(CH$_2$)$_m$—, with m being an integer of 1 to 3; and —C(CH$_3$)$_2$—, and which comprises one or more aromatic groups;
- so as to obtain a compound (I) having groups G/G' of formula -E-Ar—X" as detailed above.

According to a sixth variant, the method of the invention comprises reacting in Step (a) a compound of formula (II) with G" being a precursor of G/G' and G"'=H, and said method comprises a Step (6V-C) comprising:
- a Step (6V-C-1) of reacting compound of formula (IV) with G"=H with (ii) an acyl group using a X—C(O)—R"$_{hyc}$ reactant, with X=Cl, Br, and R"$_{hyc}$ being a C$_1$-C$_{18}$ possibly substituted hydrocarbon group, which comprises one or more of groups of formula: —(CH$_2$)$_m$—, with m being an integer of 1 to 3; —C(CH$_3$)$_2$—, and —SO$_2$—, and which comprises one or more aromatic groups;
- so as to obtain a compound of formula (I) having groups G/G' of formula -E-Ar—X" as detailed above, with E being —C(O)—.

According to a seventh variant, the method of the invention comprises reacting in Step (a) a compound of formula (II) with G" being a precursor of G/G' and G"=H, and said method comprises a Step (7V-C) comprising:
- a Step (7V-C-1) of reacting compound of formula (IV) with G"=H with (iii) a sulfonyl halide reactant of formula X—S(O)$_2$—R'"$_{hyc}$, with X=Cl, Br, and R'"$_{hyc}$ being a C$_1$-C$_{18}$ possibly substituted hydrocarbon group, which comprises one or more aromatic groups;
- so as to obtain a compound of formula (I) having groups G/G' of formula -E-Ar—X" as detailed above, with E being —S(O)$_2$—.

The invention further pertains to certain novel perfluorocyclobutyl-containing monomers of formula (I) as above detailed, whereas G and G' are groups of formula -E-Ar—X", with X" being hydrogen, —OH, —X$^{oo}$, —C(O)X$^\#$ with X$^\#$ being —OH, or being —X$^{oo}$; with X$^{oo}$ being a halogen selected from Cl, Br, I, in particular —Cl; -E- being a divalent bridging group selected from the group consisting of a bond, a C$_1$-C$_6$ carbon-containing bridging group or a sulphur-containing bridging group; exemplary embodiments of -E- are notably: —(CH$_2$)$_m$—, with m being an integer of 1 to 3; —C(O)—, —C(CH$_3$)$_2$—, and —SO$_2$—; —Ar— being a divalent aromatic group, in particular a (optionally substituted) phenyl group (-Ph-), e.g. whereas the linking bonds in -Ph- may be in ortho, meta or para position with respect to each other, preferably in para position Still, the invention pertains to a method of making a polycondensation polymer, this method comprising:
- making a compound of formula (I) according to the method as above detailed; and
- polycondensing the same with at least one additional compound possessing at least two reactive groups able to react through condensation reaction with groups G and G' of compound of formula (I).

According to certain embodiments, the polycondensation polymer is a polymer selected from the group consisting of a polyimide a polyamide and a polyamideimide and the compound of formula (I) is a compound wherein G and G' are groups of formula —NH$_2$; according to this embodiment, the compound of formula (I) may be polycondensed with a polycarboxylic acid selected from the group consisting of:
- di-carboxylic acids (or derivative thereof), generally leading to a polyamide polymer;
- a polycarboxylic acid comprising at least two alpha,beta or ortho carboxylic acid groups (or derivatives thereof, in particular in their acid anhydride form) and at least an additional carboxylic acid group (or derivative thereof), generally leading to a polyamideimide polymer; and a polycarboxylic acid comprising two couples of alpha, beta or ortho carboxylic acid groups (or derivatives thereof, in particular in their acid anhydride form), generally leading to a polyimide polymer.

It is further understood that additional di-amino compounds may be further used, so as to generate copolymers of compound of formula (I) with other units deprived from the perfluorocyclobutyl group; the relative amount of units derived from compounds of formula (I) may represent at least 1%, preferably at least 2%, more preferably at least 5%; and/or at most 50%, preferably at most 30%, more preferably at most 20%, even more preferably at most 15% by moles, with respect to the total moles of recurring units of copolymers of compound of formula (I).

Should the disclosure of any patents, patent applications, and publications which are incorporated herein by reference conflict with the description of the present application to the extent that it may render a term unclear, the present description shall take precedence."

The present invention will be now described in more details with reference to the following examples, whose purpose is merely illustrative and not intended to limit the scope of the invention.

Preparative Example 1

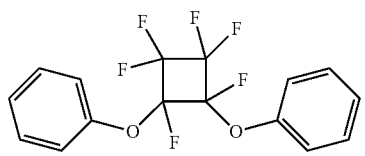 [SMILES: FC1(F)C(F)(F)C(F)(Oc2ccccc2)C1(F)Oc1ccccc1]

Step (a) and (b): Synthesis of Ph-O—CF=CF$_2$ (TFVOB-H) and Dimerization to Ph-O—C$_4$F$_6$—O-Ph (DPhFCB—H)

A sample of 50 g of phenol was loaded in a glass flask together with 210 g of 10% wt aqueous solution of NaOH. The solution was stirred for 25 minutes and than water was completely removed using a rotavapor obtaining a dry white powder of sodium phenolate. 390 g of THF were used to solubilize the sodium phenolate. The solution obtained was transferred into 600 mL stainless steel autoclave and, after purging with nitrogen and final vacuum at 0.3 bar, was maintained at a constant pressure of 10 bar of C$_2$F$_4$ for 6 h at 65° C. under stirring. The obtained solution was transferred into a separator funnel and washed with 1800 ml of distilled water. The organic phase was separated and distilled under vacuum from 155 mbar down to 2 mbar obtaining 64 g of a colorless liquid that was characterized via F19 and H1 NMR and identified as Trifluorovinyl oxybenzene (TFVOB-H) having a purity of 96%. Global molar yield was 66%.

Step (b): Dimerization to Ph-O—C$_4$F$_6$—O-Ph (DPhFCB—H)

TFVOB-H obtained was transferred into a stainless steel bomb, pressurized with 3 bar of nitrogen and heated at 180° C. for 42 h. After that time the bomb was cooled, the product obtained was recovered and vacuum distilled at 2 mbar obtaining 59 g of product that was characterized via 19F-NMR and 1H-NMR and identified as [(hexafluorocyclobutane diyl)bis(oxy)]dibenzene (DPhFCB—H) with a purity of 99.2%.

Step (c)

(C-1): Synthesis of O$_2$N-Ph-O—C$_4$F$_6$—O-Ph-NO$_2$ (DPhFCB—NO$_2$)

To a well stirred solution of DPhFCB-1 (50 g, 0.144 mol) in DCM (250 mL) at 0° C., mixed acid i.e a mixture of HNO$_3$ (46 g) and H$_2$SO$_4$ (138 g) was added dropwise via dropping funnel over a period of 45 minutes. The reaction mass was stirred at 20° C. for another 1.5 hour after the complete addition of the acid mixture. After the completion of the reaction, it was diluted with ice cold water (1 litre) and neutralized using Sodium bicarbonate. The compound was extracted using Ethylacetate (400 mL×3). The organic layer was dried over sodium sulfate and concentrated by rotary evaporation. The pure compound DPhFCB—NO$_2$ was isolated after crystallization from Ethylacetate as white crystals (Yield 70%, 44 g), Purity>98% (GC).

(C-2): Synthesis of H$_2$N-Ph-O—C$_4$F$_6$—O-Ph-NH$_2$

To a well stirred solution of DPhFCB—NO$_2$ (20 g, 0.045 mol) in MeOH (250 mL), 10% Pd/C (0.575 g) was added. Hydrazine Hydrate Solution (80%, 21.56 mL) was added using dropping funnel over a period of 1 hour. After the completion of the reagent addition, the reaction mixture was refluxed for another 1.5 h. The solution was then cooled to room temperature and filtered through celite. The filtrate was evaporated to remove MeOH. Obtained resinous mass was dissolved in DCM and was washed with water to remove excess hydrazine hydrate. The organic layer was dried over sodium sulfate and evaporated to dryness. The final product DPhFCB—NH$_2$ was colourless gummy liquid (Yield 85%, 14.8 g), Purity 98% (HPLC).

Preparative Example 2

Step (a): A sample of 40.04 g of 4-Bromo-phenol was loaded in a glass flask together with 109 g of 10% wt aqueous solution of NaOH. The solution was stirred for 25 minutes and then water was completely removed using a rotavapor obtaining a pale yellow powder of sodium 4-Bromo-phenolate. 282 g of THF were used to solubilize the sodium 4-Bromo-phenolate. The solution obtained was transferred into a 600 mL stainless steel autoclave and, after purging with nitrogen and final vacuum at 0.3 bar, was maintained at a constant pressure of 10 bar of C$_2$F$_4$ for 6 h at 65° C. under stirring. The obtained solution was transferred into a separator funnel and washed with 1800 ml of distilled water. The organic phase was separated and vacuum distilled from 17 mbar down to 1 mbar obtaining 43 g of a colorless liquid that was characterized via NMR F19 and H1 and identified as trifluorovinyloxy-4-bromo-benzene (TFVOB-Br) with a purity of 87%. Molar yield was 63%.

Step (b): TFVOB-Br obtained was transferred into a stainless steel bomb, pressurized with 3 bar of nitrogen and heated at 180° C. for 42 h.

After that time the bomb was cooled, the product obtained was recovered and vacuum distilled at 0.27 mbar obtaining 28 g of final product that was characterized via $^{19}$F-NMR and $^1$H-NMR and identified as [(hexafluorocyclobutane diyl)bis(oxy)]dibenzenebromide (DPhFCB—Br) with a purity of 99.5%.

Preparative Example 3

Step (a) and (b): See Preparative Example 2

Step (c1): Synthesis of NC-Ph-O—C$_4$F$_6$—O-Ph-CN (DPhFCB—CN)

To a well stirred solution of DPhFCB—Br (3 g, 5.92 mmol) in NMP (10 mL) at room temperature, K$_4$Fe(CN)$_6$ (dry)(1.09 g, 2.96 mmol), Na$_2$CO$_3$ (1.25 g, 11.79 mmol), Pd(OAc)$_2$ (0.265 g, 1.18 mmol) was added. The reaction mass was then stirred at 120° C. for another 24 hours under nitrogen. After the completion of the reaction, it was diluted with water (100 mL). The compound was extracted using Ethyl acetate (50 mL×3). The organic layer was dried over sodium sulfate and concentrated by rotary evaporation. The pure compound was isolated as colourless liquid after column chromatography (Yield 80%).

Step (c2): Synthesis of HOOC-Ph-O—C$_4$F$_6$—O-Ph-COOH (DPhFCB—COOH)

To a well stirred solution of DPhFCB—CN (2 g, 5.05 mol) in ″BuOH (6 mL), KOH (2.8 g, 44.6 mol) was added. The reaction mixture was refluxed for 4 h. The solution was then cooled to room temperature and diluted with water (10 mL). The solution was then acidified with dil. HCl. The precipitate was filtered and washed with water (10 mL) for 4 times to remove the traces of mineral acid. Desired product was isolated as white solid (Yield 60%).

Polymerization Example 4: Synthesis of Polyimide from DPhFCB—NH$_2$ and Pyromellitic Acid A double walled round bottom flask with temperature controller was charged with 0.658 G (2.59 mmol) of 98% pyromellitic acid and 5.5 mL of pure methanol. The reaction medium was stirred and heated to 50° C. while flushing gently with nitrogen. In a 50 mL round-bottom flask, 1.0 g (2.645 mmol) of 98% DPhFCB—NH$_2$ was dissolved in 8.5 mL of pure methanol at ambient temperature. This solution was then placed in a dropping funnel connected to the double walled round-bottomed flask and added dropwise over 15 minutes to the methanolic solution of pyromellitic acid. The reaction medium was maintained with vigorous stirring for 1 hour 30 minutes at 50° C. under nitrogen. The temperature was then reduced to 25° C. and stirred for another 30 minutes to ease further precipitation. The salt powder was recovered by filtration on a Buchner funnel, and was washed with ice cold methanol 3 times to remove unreacted starting material. The salt was then ground and dried under vacuum overnight at 60° C. The melting temperature of the salt is 240° C.

The DPhFCB—NH$_2$—PMA salt powder was placed in flask attached to a Kugelrohr, and rotated (rpm 30) under gentle flushing with nitrogen. The flask is the heated at 220° C. and rotated for 2 hours and at 240° C. for 1 hour. The PI powder obtained was found to be yellow. TGA analysis showed 5% weight loss at 506° C. temperature. FTIR analysis of the polyimide powder showed the characteristic absorption bands of imide functions at 1390, 1720 and 1783 cm$^1$ and the absence of absorption bands characteristic of amine functions is noted.

Polymerization Example 5: Synthesis of Polyimide from DPhFCB—NH$_2$ and Biphenyl Tetracarboxylic Acid (BPTA)

A double walled round bottom flask with temperature controller is charged with 0.856 G (2.59 mmol) of 98% Biphenyltetracarboxylicacid (BPTA) and 12.6 mL of pure methanol. The reaction medium was stirred and heated to 50° C. while flushing gently with nitrogen. In a 50 mL round-bottom flask, 1.0 g (2.645 mmol) of 98% DPhFCB—NH$_2$ was dissolved in 12.6 mL of pure methanol at ambient temperature. This solution was then placed in a dropping funnel connected to the double walled round-bottomed flask and added dropwise over 15 minutes to the methanolic solution of BPTA. The reaction medium is maintained with vigorous stirring for 1 hour 30 minutes at 50° C. under nitrogen. The temperature was then reduced to 25° C. and stirred for another 30 minutes to ease further precipitation. The salt powder was recovered by filtration on a Buchner funnel, and was washed with ice cold methanol 3 times to remove unreacted starting material. The salt was then ground and dried under vacuum overnight at 60° C. The melting temperature of the salt was found to be 228° C.

The DPhFCB—NH$_2$—BPTA salt powder was placed in flask attached to a Kugelrohr, and rotated (rpm 30) under gentle flushing with nitrogen. The pressure was equal to atmospheric pressure. The flask was then heated at 200° C. and rotated for 9 hours. The PI powder obtained was found to be yellow. TGA analysis showed 5% weight loss at 496° C. temperature. FTIR analysis of the PI powder showed the characteristic absorption bands of imide functions at 1375, 1719 and 1777 cm$^{-1}$ and the absence of absorption bands characteristic of amine functions was noted. The DSC shows melting at 348° C. (enthalpy of fusion 36.2 J/g) and glass transition temperature of 225° C.

Polymerization Example 6: Synthesis of Polyimide from DPhFCB—NH$_2$ and 4,4'-(Hexafluoroisopropylidene) Diphthalic Anhydride (6-FDA)

In a typical polymerization, a three-necked round bottom flask, equipped with magnetic stirrer, nitrogen inlet/outlet was charged with DPhFCB—NH$_2$ (0.851 g, 2.25 mmol) and N-methyl-2-pyrolidone (NMP) (16 mL). To this stirring solution, 4,4'-(Hexafluoroisopropylidene)diphthalic anhydride (6-FDA) (1.0 g, 2.25 mmol) was added in portion and the resulting solution was allowed to stir at room temperature for 24 h under inert atmosphere. The obtained poly (amic acid) solution was poured on a flat PTFE petri-dish and heated in a vacuum oven at 70° C. for 24 h, followed by 100-275° C. (temperature ramp: 25° C./1.0 h) and finally at 300° C. for 1.0 h to obtain transparent film. TGA analysis showed 5% weight loss at 496° C. temperature. FTIR analysis of the polyimide film showed the characteristic absorption bands of imide functions at 1375, 1719 and 1777 cm$^{-1}$. The DSC showed glass transition temperature at 246° C.

The invention claimed is:

1. A method for manufacturing a compound of general formula [formula (I)]:

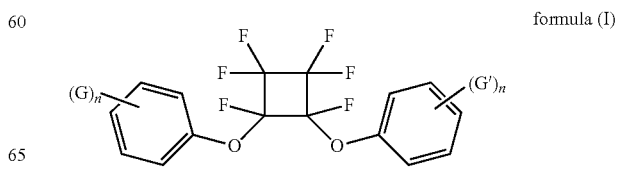

formula (I)

wherein each of G and G', equal to or different from each other, is independently selected from the group consisting of halogens selected from F, Cl, Br, I;

—NRH$^1$RH$^2$, with RH$^1$ and RH$^2$ being independently H or a C$_1$-C$_6$, hydrocarbon group;

—OH;

nitrile group of formula —CN and nitro group of formula —NO$_2$;

—COY, with Y being —X, with X being a halogen selected from F, Cl, Br, I; —OH; —ORH$^3$, —NRH$^1$RH$^2$, with RH$^3$ being a C$_1$-C$_{12}$ hydrocarbon group; and RH$^1$ and RH$^2$ having the meaning detailed above;

—SO$_2$Y', with Y' being —OH, or being —X', with X' being a halogen selected from F, Cl, Br, I;

-E-Ar—X", with X" being hydrogen, —OH, —X$^{oo}$, —C(O)X$^{\#}$ with X$^{\#}$ being —OH, or being —X$^{oo}$; with X$^{oo}$ being a halogen selected from F, Cl, Br, I;

-E- being a divalent bridging group selected from the group consisting of a bond, a C$_1$-C$_6$ carbon-containing bridging group; a sulphur-containing bridging group, a group of formula

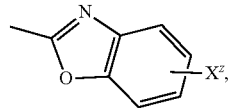

with X$^z$ being —NH$_2$; —NO$_2$; —OH, —X$^{oo}$, —C(O)X$^{\#}$ with X$^{\#}$ being —OH, or being —X$^{oo}$; with X$^{oo}$ being a halogen selected from F, Cl, Br, I;

each of n, equal to or different from each other, is an integer of 1 to 3, said method comprising:

Step (a): a step of reacting an anion of formula [formula (II)]:

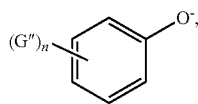

formula (II)

wherein G" is a group G or G', as described above, or is a precursor thereof, with tetrafluoroethylene at a temperature of at most 115° C. and at a pressure of at least 4 bar, so as to obtain a compound of formula [formula (III)]:

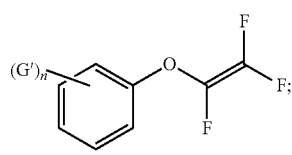

formula (III)

Step (b): a step of dimerizing at least one compound of formula (III) obtained from step (a) by thermal treatment at a temperature exceeding 150° C., so as to obtain a compound of formula [formula (IV)]:

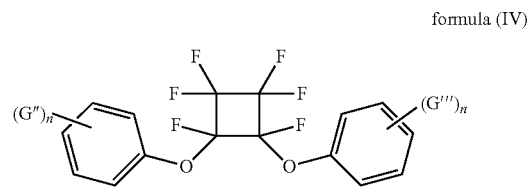

formula (IV)

wherein each of G" and G'" is a group G or G', as described above, or is a precursor thereof, being understood that when G" and G'" are a group G or G' as detailed above, compound of formula (IV) qualifies as a compound of formula (I); and Step (c): optionally, a step of reacting compound of formula (IV) in appropriate conditions to transform precursor groups G" and G'" of formula (IV) into groups G and G' so as to obtain compound of formula (I) above.

2. The method of claim 1, wherein providing an anion of formula (II) is effected by reacting corresponding phenol derivative of formula (IIp) with a base:

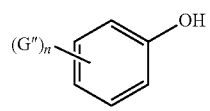

formula (IIp)

wherein n and G" have the same meaning as indicated in claim 1, and wherein the said base is selected from hydroxides of alkali metal or alkali metal.

3. The method of claim 1, wherein compound (II) is provided in Step (a) in substantially anhydrous form comprising an amount of residual water of less than 500 ppm.

4. The method of claim 1, wherein Step (a) is carried out in the presence of a polar organic solvent.

5. The method of claim 4, wherein in Step (a), reaction temperature is kept at a temperature of at most 115° C.; and/or wherein in Step (a), reaction pressure is of at least 4 bar, and/or at most 30 bar.

6. The method according claim 1, wherein Step (b) is carried out using only one compound of formula (III), and/or wherein reaction in Step (b) is carried out under inter atmosphere at a pressure of exceeding atmospheric pressure and/or at a reaction temperature of at least 155° C.

7. The method of claim 1, wherein G" in formula (III) is a group G or G', and wherein the method of the invention leads through the sequence of Step (a) and Step (b) to the target product of formula (I).

8. The method of claim 1, wherein G" in formula (III) is different from group G and G'.

9. The method of claim 8, wherein G" is a hydrogen, and Step (c) comprises at least one step selected from the group consisting of:

a step (C-1) of electrophilic aromatic substitution, wherein said hydrogen G" atom of a compound of formula (IV) is reacted with an electrophile selected from the group consisting of:

(i) a X—R'$_{hyc}$ reactant, wherein X is Cl or Br, bound to a sp$^3$-hybridized carbon of R'$_{hyc}$ group, and R'$_{hyc}$ being a C$_1$-C$_{18}$ optionally substituted hydrocarbon group including said sp$^3$-hybridized carbon, which optionally comprise one or more of groups of formula: —(CH$_2$)$_m$—, with m being an integer of 1 to 3;

—C(O)—, —C(CH$_3$)$_2$—, or —SO$_2$—, and which optionally comprise one or more aromatic groups;
(ii) a X—C(O)—R"$_{hyc}$ reactant, wherein X is Cl or Br, and R"$_{hyc}$ being a C$_1$-C$_{18}$ optionally substituted hydrocarbon group, which optionally comprise one or more of groups of formula: —(CH$_2$)$_m$—, with m being an integer of 1 to 3; —C(O)—, —C(CH$_3$)$_2$—, or —SO$_2$—, and which optionally comprise one or more aromatic groups;
(iii) a X—SO$_2$—R*$_{hyc}$ reactant, wherein X is Cl or Br, and R*$_{hyc}$ being a C$_1$-C$_{18}$ optionally substituted hydrocarbon group, which optionally comprise one or more of groups of formula: —(CH$_2$)$_m$—, with m being an integer of 1 to 3; —C(O)—, —C(CH$_3$)$_2$—, or —SO$_2$—, and which optionally comprise one or more aromatic groups;
a step (C-2) of sulfonation of a compound of formula (IV), which would lead to compounds of formula (I) having groups G and G' of formula —SO$_2$Y';
a step (C-3) of nitration optionally followed by a step of reduction to lead to compounds of formula (I) having G and G' of formula —NRH$^1$RH$^2$.

10. The method of claim 8, wherein G" is a halogen selected from F, Cl, Br, I, and wherein Step (c) comprises at least one step selected from the group consisting of:
a step (C-4) of nucleophilic substitution, by reaction of a compound of formula (IV) with:
(j) an alkali hydroxide, so as to obtain a compound of formula (I) with G and G' being-OH;
(jj) a CN-containing compound, leading to the corresponding CN-substituted compound of formula (I), which (jj-1) is optionally hydrolysed to provide for compounds of formula (I), wherein G and G' are groups of formula —COY, or (jj-2) is optionally reacted with an ortho-amino-phenol derivative of formula

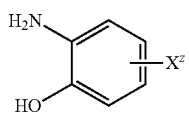

so as to provide for compounds of formula (I) wherein G and G' are groups of formula

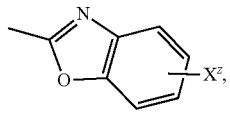

with X$^z$ being —NH$_2$; —NO$_2$; —OH, —X$^{oo}$, —C(O)X$^\#$ with X$^\#$ being —OH, or being —X$^{oo}$; with X$^{oo}$ being a halogen selected from F, Cl, Br, I;

(jjj) an alkali (alkyl)amide, leading to compounds of formula (I) wherein G and G' are groups of formula —NRH$^1$RH$^2$;
a step (C-5) of reaction of the compound of formula (IV) with Mg or Li, to form corresponding organo-magnesium or organo-lithium compounds of formula (I) wherein G and G' are groups of formula —MgX$^{Mg}$ or —Li, with X$^{Mg}$ being a halogen, which are optionally further reacted for generating a compound of formula (I) wherein G and G' are groups of formula -E-Ar—X', with X" being hydrogen or halogen.

11. The method of claim 8, wherein G" is C$_1$-C$_3$ alkyl group, and wherein Step (c) comprises at least one step selected from the group consisting of:
a Step (C-6) of oxidation of a compound of formula (IV) to provide for compounds of formula (I) wherein G and G' are groups of formula —COY, wherein said groups of formula —COY are optionally reacted with an ortho-amino-phenol derivative of formula

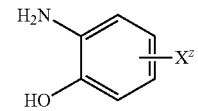

so as to provide for compounds of formula (I) wherein G and G' are groups of formula

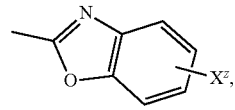

with X$^z$ being —NH$_2$; —NO$_2$; —OH, —X$^{oo}$, —C(O)X$^\#$ with X$^\#$ being —OH, or being —X$^{oo}$; with X$^{oo}$ being a halogen selected from F, Cl, Br, I.

12. The method of claim 8, wherein G" is a C$_1$-C$_3$ alkoxy group, and wherein Step (c) comprises at least one step selected from the group consisting of:
a Step (C-7) of hydrolysis of a compound of formula (IV), so as to provide for compounds of formula (I) wherein G and G' are groups of formula —OH.

13. A method of making a polycondensation polymer, this method comprising:
making the compound of formula (I) according to the method of claim 1; and
polycondensing the same with at least one additional compound possessing at least two reactive groups able to react through condensation reaction with groups G and G' of compound of formula (I).

* * * * *